US006895271B2

(12) United States Patent  (10) Patent No.: US 6,895,271 B2
Henley  (45) Date of Patent: May 17, 2005

(54) IONTOPHORETIC DRUG DELIVERY ELECTRODES AND METHOD

(75) Inventor: Julian L. Henley, Guilford, CT (US)

(73) Assignee: Biophoretic Therapeutic Systems, LLC, Framingham, MA (US)

( * ) Notice: Subject to any disclaimer, the term of this patent is extended or adjusted under 35 U.S.C. 154(b) by 0 days.

(21) Appl. No.: 10/647,295

(22) Filed: Aug. 26, 2003

(65) Prior Publication Data

US 2004/0039328 A1 Feb. 26, 2004

Related U.S. Application Data

(60) Continuation of application No. 09/653,992, filed on Sep. 1, 2000, now abandoned, which is a division of application No. 09/153,640, filed on Sep. 15, 1998, now Pat. No. 6,148,231.

(51) Int. Cl.[7] ............................. A61N 1/30; A61M 31/00
(52) U.S. Cl. ......................................... 604/20; 604/501
(58) Field of Search .............................. 604/20, 22, 19, 604/289, 500, 501; 601/1, 2; 607/115, 120, 149, 152, 98

(56) References Cited

U.S. PATENT DOCUMENTS

| 206,474 A | 7/1878 | Morel |
| 279,524 A | 6/1883 | Beaty |
| 484,522 A | 10/1892 | McBride |

(Continued)

FOREIGN PATENT DOCUMENTS

| AT | OE 0232642 | 3/1964 | .................. 604/20 |
| EP | 0230749 | 8/1987 | .................. 604/20 |
| EP | 0309093 A1 | 3/1989 | .................. 604/20 |

(Continued)

OTHER PUBLICATIONS

"Iontophoresis for Surface Local Anesthesia," Gangarosa, JADA, vol. 88, pp. 125–128, Jan. 1974.
"Conductivity of Drugs Used for Iontophoresis," Gangarosa et al., Journal of Pharmaceutical Sciences, vol. 87, No. 10, pp. 439–1443, Oct., 1978.

(Continued)

Primary Examiner—Sharon Kennedy
(74) Attorney, Agent, or Firm—Nixon & Vanderhye

(57) ABSTRACT

Non-reusable, medicament-dispensing applicator electrodes adapted for use with an iontophoresis device for facilitating delivery of medication across the cutaneous membrane into adjacent underlying tissues and blood vessels. The embodiments of the iontophoresis electrode include an open mesh having cells in the medicament dispensing portions of the electrode which retain a medicament in the form of liquid, gel or ointment. The cells are adapted to contain and iontophoretically dispense and deliver medicament formulations, which have been previously approved for therapeutic use by cognizant regulatory authorities obviating the need for reformulation. The medicament-dispensing electrodes are composite or unitary in construction and may be useful in the treatment of acne and also genital herpes simplex infection which produces cutaneous lesions, including lesions above and below the waist. The delivery electrode, when used in accordance with the medicated electrode and method described herein, demonstrated >90% treatment efficacy in clinical trials for the treatment of genital herpes. In a particularly preferred embodiment, the dispensing electrode is adapted to be worn similarly to a glove thereby enabling the user to tactily position the medicament delivery electrode to make contact with the area to be treated; receiving current for iontophoretic transdermal delivery of medicament from a wrist-worn current driver. The electrode may also comprise a portion of one or more fingers of a glove or a whole palm to cover a larger area for self treatment. A glove having a large electrode area can be driven by a single current or a multichannel source such as described in prior patents by the present inventor.

4 Claims, 5 Drawing Sheets

U.S. PATENT DOCUMENTS

| | | | |
|---|---|---|---|
| 600,290 A | 3/1898 | Muir | |
| 1,967,927 A | 7/1934 | Deustch | 604/20 |
| 2,047,308 A | 7/1936 | Chapman | 128/799 |
| 2,123,980 A | 7/1938 | Warwick | |
| 2,126,070 A | 8/1938 | Wappler | |
| 2,834,344 A | 5/1958 | Kanai | |
| 3,019,787 A | 2/1962 | Simmons | |
| 3,048,170 A | 8/1962 | Lemos | |
| 3,107,672 A | 10/1963 | Hofmann | |
| 3,163,166 A | 12/1964 | Brant et al. | |
| 3,298,368 A | 1/1967 | Charos | |
| 3,520,297 A | 7/1970 | Bechtold | |
| 3,556,105 A | 1/1971 | Shepard | |
| 3,645,260 A | 2/1972 | Cinotti et al. | |
| 3,716,054 A | 2/1973 | Porter et al. | |
| 3,831,598 A | 8/1974 | Tice | |
| 3,848,600 A | 11/1974 | Patrick, Jr. et al. | 128/783 |
| 4,116,238 A | 9/1978 | Pettijohn | 128/172.1 |
| 4,166,457 A | 9/1979 | Jacobsen et al. | |
| 4,211,222 A | 7/1980 | Tapper | 128/803 |
| 4,292,968 A | 10/1981 | Ellis | 128/207.21 |
| 4,301,794 A | 11/1981 | Tapper | 604/20 |
| 4,325,367 A | 4/1982 | Tapper | |
| 4,383,529 A | 5/1983 | Webster | |
| 4,393,884 A | 7/1983 | Jacobs | 131/273 |
| 4,406,658 A | 9/1983 | Lattin et al. | 604/20 |
| 4,416,274 A | 11/1983 | Jacobsen et al. | 128/803 |
| 4,429,703 A | 2/1984 | Haber | 131/273 |
| 4,474,570 A | 10/1984 | Ariura et al. | |
| 4,510,939 A | 4/1985 | Brenman et al. | |
| 4,639,244 A | 1/1987 | Rizk et al. | |
| 4,655,229 A | 4/1987 | Sensabaugh, Jr. et al. | 131/273 |
| 4,665,921 A | 5/1987 | Teranishi et al. | |
| 4,689,039 A | 8/1987 | Masaki | |
| 4,702,732 A | 10/1987 | Powers et al. | |
| 4,708,716 A | 11/1987 | Sibalis | 604/20 |
| 4,735,217 A | 4/1988 | Gerth et al. | 131/273 |
| 4,747,819 A | 5/1988 | Phipps et al. | |
| 4,756,318 A | 7/1988 | Clearman et al. | 131/359 |
| 4,763,660 A | 8/1988 | Kroll et al. | 128/798 |
| 4,764,164 A | 8/1988 | Sasaki | 604/20 |
| 4,767,402 A | 8/1988 | Kost et al. | |
| 4,771,796 A | 9/1988 | Myer | 131/273 |
| 4,776,353 A | 10/1988 | Lilja et al. | 131/297 |
| 4,786,278 A | 11/1988 | Masaki | 604/20 |
| 4,787,888 A | 11/1988 | Fox | |
| 4,793,366 A | 12/1988 | Hill | 131/273 |
| 4,800,903 A | 1/1989 | Ray et al. | 131/273 |
| 4,808,152 A | 2/1989 | Sibalis | 604/20 |
| 4,813,437 A | 3/1989 | Ray | 131/273 |
| 4,820,263 A | 4/1989 | Spevak et al. | 604/20 |
| 4,821,740 A | 4/1989 | Tachibana et al. | 604/20 |
| 4,838,273 A | 6/1989 | Cartmell | |
| 4,865,582 A | 9/1989 | Sibalis | 604/20 |
| 4,907,606 A | 3/1990 | Lilja et al. | 131/273 |
| 4,913,148 A | 4/1990 | Diethelm | |
| 4,917,119 A | 4/1990 | Potter et al. | 131/273 |
| 4,919,648 A | 4/1990 | Sibalis | |
| 4,922,901 A | 5/1990 | Brooks et al. | 128/203.26 |
| 4,931,046 A | 6/1990 | Newman | 604/20 |
| 4,942,883 A | 7/1990 | Newman | 604/20 |
| 4,950,229 A | 8/1990 | Sage, Jr. | 604/20 |
| 4,953,565 A | 9/1990 | Tachibana et al. | |
| 4,957,480 A | 9/1990 | Morenings | |
| 4,979,938 A | 12/1990 | Stephen et al. | |
| 4,997,418 A | 3/1991 | DeMartini | |
| 5,002,527 A | 3/1991 | Reller et al. | |
| 5,006,108 A | 4/1991 | LaPrade | 604/20 |
| 5,019,034 A | 5/1991 | Weaver et al. | 604/20 |
| 5,037,381 A | 8/1991 | Bock et al. | |
| 5,042,975 A | 8/1991 | Chien et al. | |
| 5,047,007 A | 9/1991 | McNichols et al. | 604/20 |
| 5,053,001 A | 10/1991 | Reller et al. | 604/20 |
| 5,060,671 A | 10/1991 | Counts et al. | 131/329 |
| 5,090,402 A | 2/1992 | Bazin et al. | |
| 5,115,805 A | 5/1992 | Bommannan et al. | |
| 5,133,352 A | 7/1992 | Lathrop et al. | |
| 5,135,478 A | 8/1992 | Sibalis | |
| 5,135,479 A | 8/1992 | Sibalis et al. | 604/20 |
| 5,147,291 A | 9/1992 | Cukier | 604/22 |
| 5,160,316 A | 11/1992 | Henley | |
| 5,162,042 A | 11/1992 | Gyory et al. | |
| 5,167,242 A | 12/1992 | Turner et al. | 131/273 |
| 5,169,384 A | 12/1992 | Bosniak et al. | |
| 5,171,215 A | 12/1992 | Flanagan | 604/20 |
| 5,203,768 A | 4/1993 | Haak et al. | |
| 5,250,022 A | 10/1993 | Chien et al. | |
| 5,254,081 A | 10/1993 | Maurer et al. | 604/20 |
| 5,279,543 A | 1/1994 | Glikfeld et al. | |
| 5,284,471 A | 2/1994 | Sage, Jr. | |
| 5,298,017 A | 3/1994 | Theeuwes et al. | |
| 5,310,404 A | 5/1994 | Gyory et al. | |
| 5,312,326 A | 5/1994 | Myers et al. | |
| 5,314,502 A | 5/1994 | McNichols et al. | |
| 5,331,979 A | 7/1994 | Henley | |
| 5,354,321 A | 10/1994 | Berger | |
| 5,360,440 A | 11/1994 | Andersen | |
| 5,362,307 A | 11/1994 | Guy et al. | |
| 5,362,308 A | 11/1994 | Chien et al. | |
| 5,374,241 A | 12/1994 | Lloyd et al. | |
| 5,374,242 A | 12/1994 | Haak et al. | |
| 5,376,107 A | 12/1994 | Inagi et al. | |
| 5,391,195 A | 2/1995 | Van Groningen | |
| 5,395,310 A | 3/1995 | Untereker et al. | |
| 5,413,590 A | 5/1995 | Williamson | |
| 5,415,629 A | 5/1995 | Henley | |
| 5,421,816 A | 6/1995 | Lipkovker | |
| 5,441,936 A | 8/1995 | Houghten et al. | |
| 5,443,441 A | 8/1995 | De Claviere | |
| 5,458,569 A | 10/1995 | Kirk, III et al. | |
| 5,464,387 A | 11/1995 | Haak et al. | |
| 5,466,217 A | 11/1995 | Myers et al. | |
| 5,470,349 A | 11/1995 | Kleditsch et al. | |
| 5,494,679 A | 2/1996 | Sage, Jr. et al. | |
| 5,501,705 A | 3/1996 | Fakhri | |
| 5,514,167 A | 5/1996 | Smith et al. | |
| 5,538,503 A | 7/1996 | Henley | |
| 5,540,669 A | 7/1996 | Sage, Jr. et al. | 604/20 |
| 5,551,953 A | 9/1996 | Lattin et al. | |
| 5,558,632 A | 9/1996 | Lloyd et al. | |
| 5,562,607 A | 10/1996 | Gyory | |
| 5,589,563 A | 12/1996 | Ward et al. | |
| 5,603,693 A | 2/1997 | Frenkel et al. | |
| 5,607,461 A | 3/1997 | Lathrop | |
| 5,607,691 A | 3/1997 | Hale et al. | |
| 5,618,275 A | 4/1997 | Bock | |
| 5,658,247 A | 8/1997 | Henley | |
| 5,667,487 A | 9/1997 | Henley | |
| 5,668,170 A | 9/1997 | Gyory | |
| 5,676,648 A | 10/1997 | Henley | |
| 5,678,273 A | 10/1997 | Porcelli | |
| 5,688,233 A | 11/1997 | Hofmann et al. | |
| 5,697,896 A | 12/1997 | McNichols et al. | |
| 5,700,457 A | 12/1997 | Dixon | |
| 5,711,761 A | 1/1998 | Untereker et al. | |
| 5,713,846 A | 2/1998 | Bernhard et al. | |
| 5,722,397 A | 3/1998 | Eppstein | |
| 5,725,817 A | 3/1998 | Milder | |
| 5,733,255 A | 3/1998 | Dinh et al. | |
| 5,755,750 A | 5/1998 | Petruska et al. | |
| 5,788,666 A | 8/1998 | Atanasoska | |

| | | | |
|---|---|---|---|
| 5,794,774 A | 8/1998 | Porcelli | |
| 5,795,321 A | 8/1998 | McArthur et al. | |
| 5,797,867 A | 8/1998 | Guerrera et al. | |
| 5,830,175 A | 11/1998 | Flower | |
| 5,840,057 A | 11/1998 | Aloisi | |
| 5,846,217 A | 12/1998 | Beck et al. | |
| 5,865,786 A | 2/1999 | Sibalis et al. | 604/20 |
| 5,879,323 A | 3/1999 | Henley | |
| 5,882,676 A | 3/1999 | Lee et al. | |
| 5,899,875 A | 5/1999 | Millot | |
| 5,899,876 A | 5/1999 | Flower | 604/20 |
| 5,908,401 A | 6/1999 | Henley | |
| 5,911,319 A | 6/1999 | Porcelli et al. | |
| 5,919,155 A | 7/1999 | Lattin et al. | |
| 5,931,859 A | 8/1999 | Burke | |
| 5,935,598 A | 8/1999 | Sage et al. | |
| 5,954,684 A | 9/1999 | Flower et al. | 604/20 |
| 5,961,482 A | 10/1999 | Chien et al. | |
| 5,961,483 A | 10/1999 | Sage et al. | |
| 5,968,005 A | 10/1999 | Tu | |
| 5,968,006 A | 10/1999 | Hofmann | |
| 5,983,130 A | 11/1999 | Phipps et al. | |
| 6,004,309 A | 12/1999 | Phipps | |
| 6,004,547 A | 12/1999 | Rowe et al. | |
| 6,006,130 A | 12/1999 | Higo et al. | |
| 6,018,679 A | 1/2000 | Dinh et al. | |
| 6,023,639 A | 2/2000 | Hakky et al. | |
| 6,032,073 A | 2/2000 | Effenhauser | |
| 6,038,485 A | 3/2000 | Axelgaard | |
| 6,041,252 A | 3/2000 | Walker et al. | |
| 6,041,253 A | 3/2000 | Kost et al. | |
| 6,048,545 A | 4/2000 | Keller et al. | |
| 6,057,374 A | 5/2000 | Huntington et al. | |
| 6,101,411 A | 8/2000 | Newsome | |
| 6,148,231 A | 11/2000 | Henley | 604/20 |
| 6,148,232 A | 11/2000 | Avrahami | 604/20 |
| 6,167,302 A | 12/2000 | Millot | |
| 6,267,736 B1 | 7/2001 | McCambridge | |
| 6,385,487 B1 | 5/2002 | Henley | 604/20 |
| 6,477,410 B1 | 11/2002 | Henley et al. | |

FOREIGN PATENT DOCUMENTS

| | | | |
|---|---|---|---|
| EP | 617979 A1 | 10/1994 | |
| FR | 1445703 | 6/1966 | 604/20 |
| FR | 2 513 129 | 3/1983 | |
| GB | 0299553 | 11/1928 | 604/20 |
| JP | 3-170172 | 7/1991 | |
| SU | 654254 | 3/1979 | |
| SU | 931191 | 5/1982 | |
| SU | 1003853 | 3/1983 | |
| WO | 86/07269 | 12/1986 | 604/20 |
| WO | WO 90/06153 | 6/1990 | |
| WO | 90/08571 | 8/1990 | 604/20 |
| WO | 93/03790 | 3/1993 | 604/20 |

OTHER PUBLICATIONS

"A Pilot Study of lontophoretic Cisplatin Chemotherapy of Basal and Squamous Cell Carcinomas of the Skin," Chang et al., Arch. Dermatol., vol. 129, pp. 425–427, Apr. 1993.

"How Modem lontophoresis Can Improve Your Practice," Gangarosa at al.; Oral Surgery, No. 10, Report 2135, Oct. 1982, pp. 1027–1038.

"Postherpetic Neuralgia," Baron et al.; Brain (1993), 116, pp. 1477–1496.

"Iontophoretic Assistance of 5–Iodo–2'–Deoxyuridlne Penetration into Neonatal Mouse Skin and Effects of DNA Synthesis," Gangarosa et al., Society for Experimental Biology and MedIcine, pp. 439–443, 1977.

"Electrophoretic Evaluation of the Mobility of Drugs Suitable for Iontophoresis," Kamath et al., Math. Find., Exp. Clin. Pharmacol., 1995, 17(4): pp. 227–232.

"Transdermal Drug Delivery by Passive Diffusion and Iontophoresis: A Revlew," Singh et al.; Medicinal Research Reviews, vol.13 No. 5, 1993, pp. 570–621.

"Iontophoresis: Electrorepulsion and Electroosmosis," Guy et al., Journal of Controlled Release 64 (2000) 129–132.

"Treatment of Common Cutaneous Herpes Simplex Virus Infections," Emmert, American Family Physician, vol. 61, No. 6, Mar. 15, 2000, pp. 1697–1704.

"Gelatin–stabilised Microemulsion–Based Oranogels: Rheology and Application in Iontophoretic Transderrnal Drug Delivery," Kantaria et al., Journal of Controlled Release 60 (1999) 355–365.

"Electrorepulsion Versus Electroosmosis: Effect of pH on the Iontophoretic Flux of 5–Fluorouracil," Merino et al., Pharmaceutical Research, vol. 16, No. 6 (1999).

"Azelaic Acid: Potential as a General Antitumoural Agent," Breathnach, Medical Hypotheses (1999) 52(3) 221–226.

"Treatment of Mucocutaneous Herpes Simplex Virus Infections Unresponsive to Acyclovir with Topical Foscarnet Cream in AIDS Patients: A Phase I/II Study," Javaly et al., Journal of Acquired Immune Deficiency Syndromes 21:301–306.

"Efficacy and Safety of Azelaic Acid and Glycolic Acid Combination Therapy Compared with Tretinoin Therapy for Acne," Spellman et al., Clinical Therapeutics, vol. 20, No. 4, 1998.

"Passive Versus Electrotransport–Facilitated Transdermal Absorption of Ketorolac," Park et al., Clinical Pharmacology & Therapeutics, vol. 63, No. 3, pp. 303–315.

"Soriudine Versus Acyclovir for Treatment of Dermatomal Herpes Zoster in Human Immunodeficiency Virus–Infected Patients: Results from a Randomized, Controlled Clinical Trial," Gnann et al., Antimicrobial Agents and Chemotherapy, vol. 42, No. 5, May 1998, pp. 1139–1145.

"Azelaic Acid 20% Cream (AZELEX®) and the Medical Management of Acne Vulgaris," Gibson, Dermatology Nursing, vol. 9, No. 5, pp. 339–344.

"Sorivudine: A Promising Drug for the Treatment of Varicella–Zoster Virus Infection," Whitley, Neurology 1995; (Supp. 8), pp. S73–S75.

"Antiherpesviral and Anticellular Effects of 1–β–D–Arabinofuranosyl–E–5–(2–Halogenovinyl) Uracils," Machida et al., Antimicrobial Agents and Chemotherapy, Jul. 1981, pp. 47–52.

"Herpes Simplex," American Academy of Dermatology.

"'Common Cold' Virus Is Near," Haney, The Associated Press, Jan. 15, 2000.

"New Medicines Move to Eradicate Acne," Hemphill, The New York Times, Feb. 29, 2000.

"Warts," American Academy of Dermatology, American Academy of Dermatology, 1997, Revised 1991, 1993.

"Psoriasis," American Academy of Dermatology, 1994.

"Eczema/Atopic Dermatitis," American Academy of Dermatology, 1987, Revised 1991, 1993, 1995.

"Skin Cancer: An Undeclared Epidemic," American Academy of Dermatology, 1988, Revised 1989, 1993, 1994.

"Electrophoretically Controlled Dermal or Transdermal Application Systems With Electronic Indicators," Groning, International Journal of Pharmaceutics, 36 (1987), pp. 37–40.

"Iontophoretic Treatment of Oral Herpes," Henley et al.; Laryngoscope, vol. 94, No. 1, pp. 118–121, Jan. 1984.

"Iontophoretic Application of Idoxuridine for Recurrent Herpes Labialis: Report of Preliminary Chemical Trials," Gangarosa et al.; Meth. And Find. Exptl. Clin. Pharmacol. 1(2), pp.105–109 (1979).

"Iontophoresis of Vidarabine Monophosphate for Herpes Orolabialis," Gangarosa et al.; The Journal of Infectious Diseases, vol. 154, No.6, pp. 930–934, Dec. 1986.

"The Natural History of Recurrent Herpes Simplex Labialis," Spruance et al.; The New England Journal of Medicine, vol. 297, No. 2, pp. 69–75, Jul. 14, 1977.

"Infection with Herpes–Simplex Viruses 1 and 2," Nahmias et al.; The New England Journal of Medicine, pp. 667–674, Sep. 27, 1973.

"Anesthesia of the Human Tympanic Membrane by Iontophoresis of a Local Anesthetic," Comeau et al.; The Laryngoscope, 88:1978, pp. 277–285.

"Iontopheric Application of Drugs," Waud, J. Appl. Physiol. 23(1), 1967, pp. 128–130.

"Antibiotic Iontophoresis in the Treatment of Ear Chondritis," LaForest et al., Physical Therapy, vol. 58, No. 1, Jan. 1978, pp. 32–34.

"The Quantity and Distribution of Radiolabeled Dexamethasone Delivered to Tissue by Iontophoresis," Glass et al.; International Journal of Dermatology, vol. 19, Nov. 1980, pp. 519–525.

"Iontophoretic Application of Antiviral Chemotherapeutic Agents," Hill et al., Annals New York Academy of Sciences, pp. 604–612.

"Ocular Iontophoresis," Hill et al. Paper, Louisiana State University Medical Center, School of Medicine, New Orleans, Louisiana, pp. 331–354.

"Iontophoretic Application of Adenine Arabinoside Monophosphate to Herpes Simplex Virus Type 1–Infected Hairless Mouse Skin," Park et al.; Antimicrobial Agents and Chemotherapy, vol. 14, No. 4, Oct., 1978, pp. 605–608.

"Iontophoresis: Applications in Transdermal Medication Delivery," Costello et al.; Physical Therapy, vol. 75, No. 6, pp. 104/554–113/563, Jun. 1995.

Physical Enhancement of Dermatologic Drug Delivery: Iontophoresis and Phonophoresis,: Kassan et al.; Journal of the American Academy of Dermatology, Apr. 1996, pp. 657–666.

"Iontophoresis and Herpes Labialis," Boxhall et al.; The Medical Journal of Australia, May 26, 1984, pp. 686–687.

"A Method of Antibiotic Administration in the Burn Patient," Rapperport et al.; Plastic and Reconstructive Surgery, vol. 36, No. 5, pp. 547–552.

"Iontophoresis for Enhancing Penetration of Dermatologic and Antiviral Drugs," Gangarosa et al., Journal of Dermatology, vol. 22, No. 11, pp. 865–875, Nov. 1995.

"Iontophoretic Treatment of Harpetic Whitlow," Gangarosa et al., Arch. Phys. Med. Rehabil., vol. 70, Apr. 1989.

"Iontophoretic Application of Antiviral Drugs," Gangarosa et al., Proceedings of an International Symposium held in Tokushima City, Japan, pp. 200–204, Jul. 27–30, 1981.

"Iontophoretic Application of Adenine Arabinoside Monophosphate for the Treatment of Herpes Simplex Virus Type 2 Skin Infections in Hairless Mice," Gangarosa, The Journal of Infectious Diseases, vol. 140, No. 6, 1014, Dec. 1979.

"Effect of Iontophoretic and Topical Application of Antiviral Agents in Treatment of Experimental HSV–1 Keratitis in Rabbits," Kwon et al., Investigative Ophthalmology & Visual Science, vol. 18, No. 9, pp. 984–988, Sep., 1979.

"Acyclovir and Vidarabine Monophosphate: Comparison of Iontophoretic and Intravenous Administration for the Treatment of HSV–1 Stromal Keratitis," Hill et al., The American Journal of Medicine, Acyvlovir Symposium, pp. 300–304.

"Thymine Arabinoside (Ara–T) Topical and Iontophoretic Applications for Herpes Simplex Virus Type 1 and Type 2 Skin Infections in Hairless Mice," Hill et al., Meth. And Find. Exptl. Clin. Pharmacol. 6(1). pp. 17–20, 1984.

"Iontophoresis Enhances the Transport of Acyclovir Through Nude Mouse Skin by Electrorepulsion and Electroosmosis," Volpato et al., Pharmaceutical Research, vol.12, No. 11, pp. 1623–1627, 1995.

"Early Application of Topical 15% Idoxuridine in Dimethyl Sulfoxide Shortens the Course of Herpes Simplex Labialis: A Multicenter Placebo–Controlled Trial," Spruance et al., The Journal of Infectious Diseases, 1990; 161; pp. 191–197.

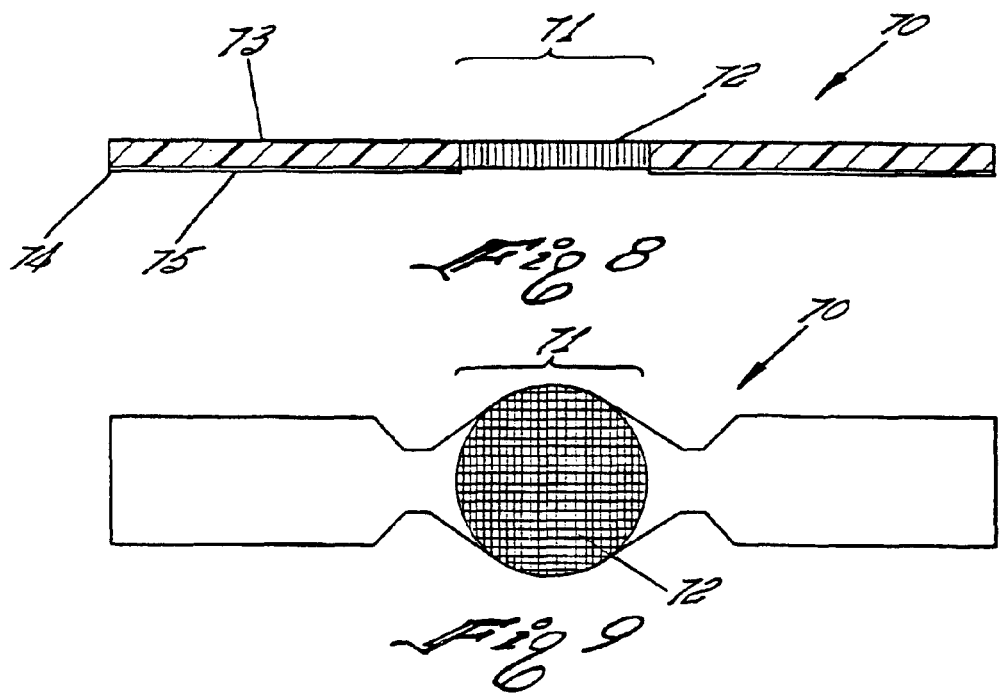
Fig 8
Fig 9
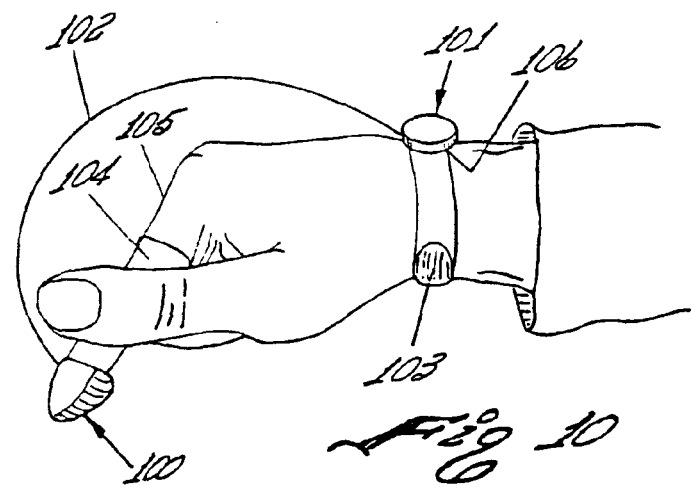
Fig 10
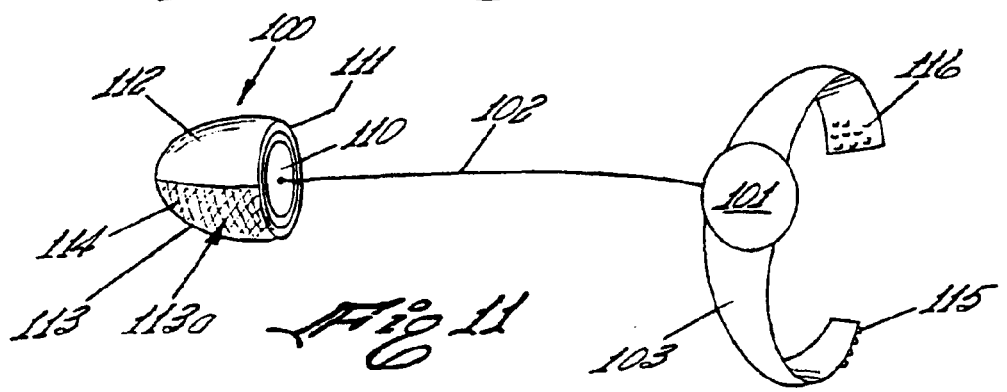
Fig 11

IONTOPHORETIC DRUG DELIVERY ELECTRODES AND METHOD

RELATED APPLICATIONS

This application is a continuation of application Ser. No. 09/653,992, filed Sep. 1, 2000 abandoned, which in turn was a divisional of application Ser. No. 09/153,640, filed Sep. 15, 1998, now U.S. Pat. No. 6,148,231, issued Nov. 14, 2000, the disclosures of which are incorporated herein by reference.

BACKGROUND OF THE INVENTION

1. Field of the Invention

This invention relates generally to the transdermal electrokinetic mass transfer of medication into a diseased tissue, and, more specifically, to a medicament containing iontophoresis electrode for the delivery of medication across the skin and into diseased tissues and blood vessels adjacent to the delivery site.

2. Prior Art

Iontophoresis has been employed for several centuries as a means for applying medication locally through a patient's skin and for delivering medicaments to the eyes and ears. The application of an electric field to the skin is known to greatly enhance the skin's permeability to various ionic agents. This permeability change has been used, for example, to enhance transcutaneous transport of glucose for monitoring blood glucose levels. The use of iontophoretic transdermal delivery techniques has obviated the need for hypodermic injection for many medicaments, thereby eliminating the concomitant problems of trauma, pain and risk of infection to the patient.

Iontophoresis involves the application of an electromotive force to drive or repel oppositely charged ions through the dermal layers into a target tissue. Particularly suitable target tissue include tissues adjacent to the delivery site for localized treatment or tissues remote therefrom in which case the medicament enters into the circulatory system and is transported to a tissue by the blood. Positively charged ions are driven into the skin at an anode while negatively charged ions are driven into the skin at a cathode. Studies have shown increased skin penetration of drugs at anodic or cathodic electrodes regardless of the predominant molecular ionic charge on the drug. This effect is mediated by polarization and osmotic effects.

Regardless of the charge of the medicament to be administered, a iontophoretic delivery device employs two electrodes (an anode and a cathode) in conjunction with the patient's skin to form a closed circuit between one of the electrodes (referred to herein alternatively as a "working" or "application" or "applicator" electrode) which is positioned at the delivered site of drug delivery and a passive or "grounding" electrode affixed to a second site on the skin to enhance the rate of penetration of the medicament into the skin adjacent to the applicator electrode.

Recent interest in the use of iontophoresis for the transdermal delivery of drugs to a desired cutaneous or subcutaneous treatment site has stimulated a redesign of many of such drugs with concomitant increased efficacy of the drugs when delivered transdermally. As iontophoretic delivery of medicaments become more widely used, the opportunity for a consumer/patient to iontophoretically self-administer a transdermal dosage of medicaments simply and safely at non-medical or non-professional facilities would be desirable and practical. Similarly, when a consumer/patient travels, it would be desirable to have a personal, easily transportable apparatus available which is operable for the iontophoretic transdermal delivery of a medication packaged in a single dosage applicator. A problem which presents an impediment to potential users is the necessity for reformulating medicaments for iontophoretic delivery. Such reformulations must be approved by cognizant regulatory agencies prior to sale. This requires delay and additional expense for the manufacturer, which additional expense may be passed along to consumers. The present invention provides a disposable medicament dispensing electrode for use with a portable iontophoretic medicament delivery apparatus in which the electrode is adapted for use with the apparatus for self-administering medicament. The medicament dispensing portion of the electrode can accept, store and dispense presently approved medicament formulations.

SUMMARY OF THE INVENTION

The present invention discloses a unit dosage medicament applicator electrode adapted for use with a portable iontophoretic transdermal or transmucoscal medicament delivery apparatus for the self-administration of a unit dose of a medicament into the skin. The electrode and current supply apparatus is particularly suited for the localized treatment of herpes infections. The established treatment for recurrent genital herpetic lesions has been primarily supportive; including local topical application of anesthesia. Severe cases have been treated with systemic Acyclovir®, Zovirax® (Glaxo-Wellcome) or Famvir® (SmithKline Beecham). Some cases the condition is managed with prophylactic long-term dosing administration with a suitable antiviral agent at great expense. Systemic treatment of acute herpetic flare-ups may reduce the normal 10–12 day course of cutaneous symptoms into a 6–8 day episode. Topical treatment of lesions with Acyclovir® has not been as effective as in vitro studies would suggest. A compound which is not presently available to clinicians but has demonstrated significant anti herpetic activity is 5-iodo-2 deoxyuridine (IUDR). Both of those agents have shown limited clinical efficacy when applied topically to the herpetic lesion. It is the present inventor's contention that the limited efficacy of topical administration previously observed is, at least in part, due to the poor skin penetration of these medicaments when applied topically. The present invention discloses a mesh-like iontophoresis electrode, which contains and dispenses pre-approved formulations of those medicaments and provides improved transdermal delivery of these medicaments.

Genital herpes (usually herpes simplex II infection) afflicts many people, cause discomfort, shame, and may contribute to more severe and costly illnesses such as cervical cancer, prostate cancer, and perinatal blindness from herpetic conjunctivitis. Certain formulations containing anti-viral and/or anti-microbial drugs have been approved for topical application by the cognizant regulatory agency. Reformulation of such compositions for iontophoretic transdermal drug delivery entails significant delays before such technology is available to the public for general use. The present invention discloses a medicated iontophoresis electrode for the portable transdermal delivery of Acyclovir® (9-[(2-hydroxyethoxy)methyl]guanine) or similar anti-viral agent formulations which have already received (or may in the future receive) regulatory approval to greatly benefit these afflicted patients. In a second preferred embodiment of the invention, the medicament delivery electrode is attached to a user-wearable glove having one or more fingers or merely a finger cot covering at least a portion of one or more fingers of a user's hand.

It is an object of the present invention to provide an iontophoretic medicament delivery electrode which is adapted to be used with an iontophoresis device operable for self-administration of medicament into the skin of a person.

It is another object of the present invention to provide an improved iontophoretic transdermal drug delivery apparatus having a medicament-containing application electrode which disperses a single dosage and is disposable and non-reusable.

It is a further object of the present invention to provide an iontophoresis electrode meeting the above objectives which can receive and retain a previously approved drug formulation for dispensation by ionosonic transdermal delivery. It is still another advantage of the present invention to provide an improved disposable iontophoretic medicament applicator which meets the above objectives and which is inexpensive, safe to use and greatly increases the therapeutic efficacy of a medicament administered thereby.

The medicament-containing electrode in accordance with the present invention, together with an iontophoresis apparatus, provides a means for transdermally administering medicament dispersed in a variety of previously approved formulations directly and with high efficiency into a diseased tissue thereby providing a novel method for treating clinical conditions presenting mucocutaneous symptoms and particularly mucocutaneous Herpes Simplex viral eruptions and sequelle associated therewith.

The above objects, features and advantages of the invention are realized by the improved monopolar iontophoretic medicament applicator electrode. The objects, features and advantages of the invention will become apparent upon consideration of the following detailed disclosure of the invention, especially when it is taken in conjunction with the accompanying drawings wherein:

BRIEF DESCRIPTION OF THE DRAWINGS

FIG. 8 is a horizontal cross-sectional view of the applicator electrode of FIG. 7 taken along section line 8—8.

FIG. 9 is a bottom plan view of the applicator electrode of FIG. 7.

FIG. 10 is a perspective view of an embodiment of an iontophoresis device and a medicament dispensing applicator electrode adapted to be releasably affixed to a finger of a patient wherein the medicament dispensing portion of the electrode is an open mesh.

FIG. 11 is a perspective view of the iontophoresis device and applicator electrode of FIG. 10 wherein the applicator electrode has been removed from the patient's finger.

DESCRIPTION OF THE PREFERRED EMBODIMENT

Figure 1:
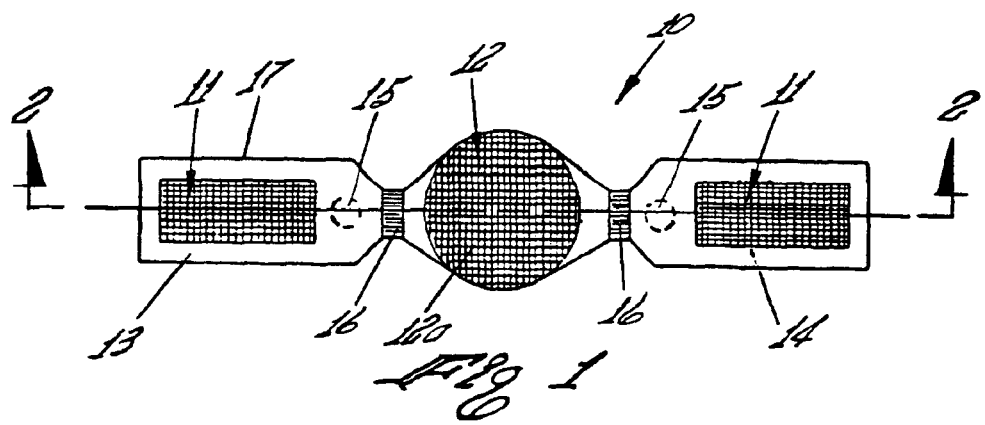
FIG. 1 is a top plan view of a first embodiment of the disposable iontophoretic medicament delivery electrode for attachment to an iontophoresis handpiece wherein the medicament dispensing portion of the electrode is an open mesh.
Figure 4:
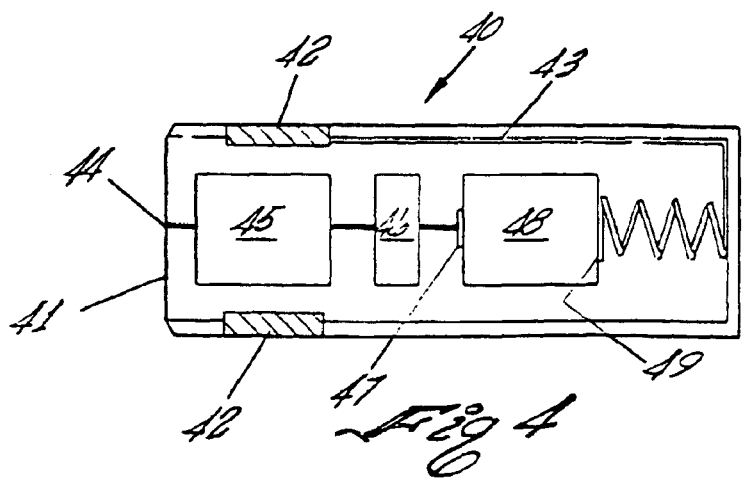
FIG. 4 is a horizontal cross-sectional plan view of an iontophoresis handpiece adapted for use with the embodiments of the medicament dispensing electrode of the present invention shown in FIGS. 1–3.

FIG. 1 shows, in top plan view, a first preferred embodiment of the hand-held iontophoretic transdermal medicament delivery apparatus of the present invention. The first preferred embodiment of the iontophoretic medicament-containing application electrode is shown at 10. The application electrode 10 is preferably disposable and non-reusable. The electrode 10 is suitable, for example, for transdermally delivering anti-viral agents such as Acyclovir® for the treatment of cold sores or genital herpes. The applicator electrode 10 is adapted for use with an iontophoresis handpiece such as the handpiece shown in FIGS. 4 and 5. In use, the applicator electrode 10 is detachably affixed to a hand-held iontophoresis handpiece 40 which handpiece presents a first electrically conductive surface 41 and a second electrically conductive surface 42. The handpiece 40 comprises a current driver 45 which receives an electrical voltage from a voltage multiplier 46 which is in electrical communication with one electrode 47 of an electrical power source 48 such as a battery. The other electrode 49 of the battery is in electrical communication with a tactile electrode 42 on the surface of the handpiece 40 which electrode is, in use, in contact with the skin of one or more fingers of a user. The electrical current from the current driver 45 is conducted through a wire or conductive strip 44 to the first electrically conductive surface 41. When the applicator electrode 10 is attached to the handpiece 40, the current passes through the conductive applicator electrode to the skin of the user, returning to the second electrically conductive element 42, or "tactile electrode" to drive the medicament 23 through the mesh-like matrix material 12 and into the user's skin. The medicament or treatment agent is contained within a viscous fluid vehicle which, in turn, is contained within a plurality of cellular apertures 12a comprising the mesh 12.

Figure 2:
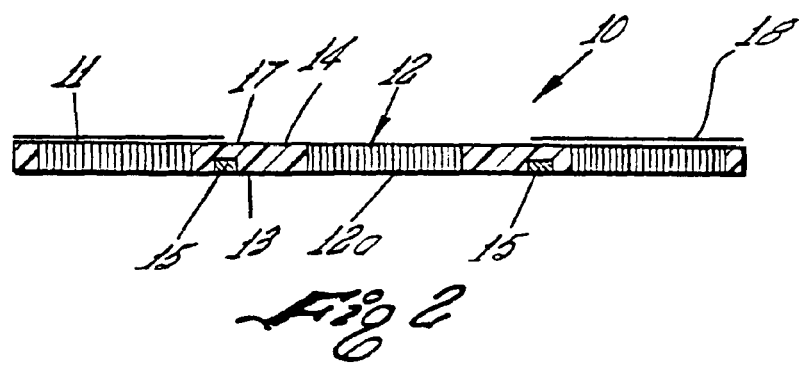
FIG. 2 is a side elevational view of a preferred embodiment of the disposable non-reusable iontophoretic application electrode for use with an iontophoresis handpiece adapted for self-administration.
Figure 3:
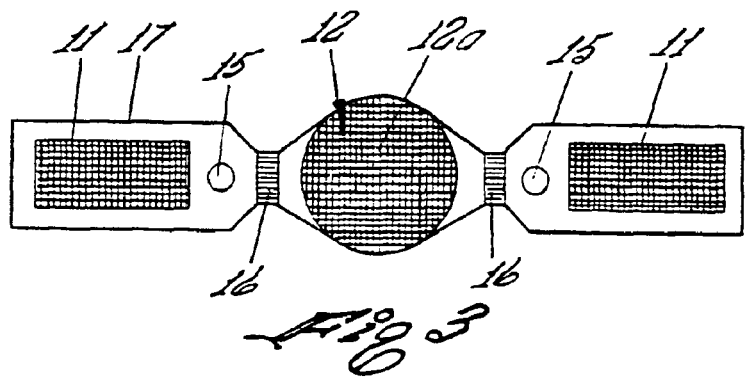
FIG. 3 is a top plan view of the iontophoresis electrode in accordance with claim 2.

The applicator electrode 10 comprises a substantially flat elongate strip having lateral ends extending from a central portion. The central medicament dispensing portion 12 is of mesh-like construction and has vertical cells dimensioned to accommodate a viscous fluid within the confines of the cellular structures. The viscous fluid contained within each of the plurality of cells 12a includes a medicament (not shown) which is in a form suitable for transport under the influence of an electrical current. The lateral ends of the applicator electrode 10 include a mesh-like tactile conductive portion 11 which contains an electrically conductive gel therewithin. The applicator electrode 10 has an upper skin-facing surface 13 and a lower, device-facing surface 14. One or a plurality of cells 12a form one or a plurality of apertures between the upper skin-facing surface 13 and the lower device-facing surface 14. The device-facing surface 14 may further include an adhesive layer 18 applied thereto suitable for releasably adhering the applicator electrode 10 to the positive (anode) or negative (cathode) pole of a iontophoresis handpiece. The positioning of the electrode's tactile conductive portion 11 on the surface of the handpiece is such that tactile conductive portion 11 makes electrical contact with the tactile electrode 42 on the handpiece. When the applicator electrode 10 is correctly positioned on the handpiece, the medicament dispensing reservoir 12 is in electrical communication with the electrically contacting element 41 on the handpiece. In addition, one or more small magnets 15 may positioned on the handpiece to activate a switch within said handpiece which turns the handpiece on and/or off. The relatively narrow, flexible areas 16 on the electrode enable the applicator electrode 10 to be bent and formed around the handpiece. FIG. 2 shows a cross-sectional view of the applicator electrode 10 of FIG. 1 taken along section lines 2—2. The material 17 forming the structural portion of the applicator electrode 10 is preferably a non-electrically conducting elastomer. A bottom view of the applicator electrode 10 of FIGS. 1 and 2 is shown in FIG. 3.

Figure 5:
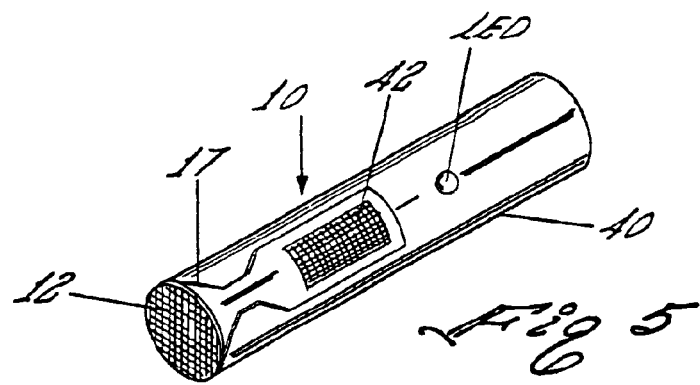
FIG. 5 is a perspective view showing the applicator electrode of FIGS. 1,3 releasably affixed to the iontophoresis handpiece of FIG. 4.
Figure 6:
FIG. 6 shows a patient preparing to self-administer medicament to a treatment site.

FIG. 5 is a perspective view of the applicator electrode 10 attached to the handpiece 40 in position for use. FIG. 6 shows a patient preparing to use the iontophoresis device for administering medicament to herpes lesions on the face. The patient 60 grasps the tactile electrode 42 with a finger 61 to make electrical communication therewith. The patient then touches the tip 12 of the applicator electrode 10 to the lesion 63 thereby completing the electrical circuit and the resulting current flow driving the medicament into the skin.

Figure 7:
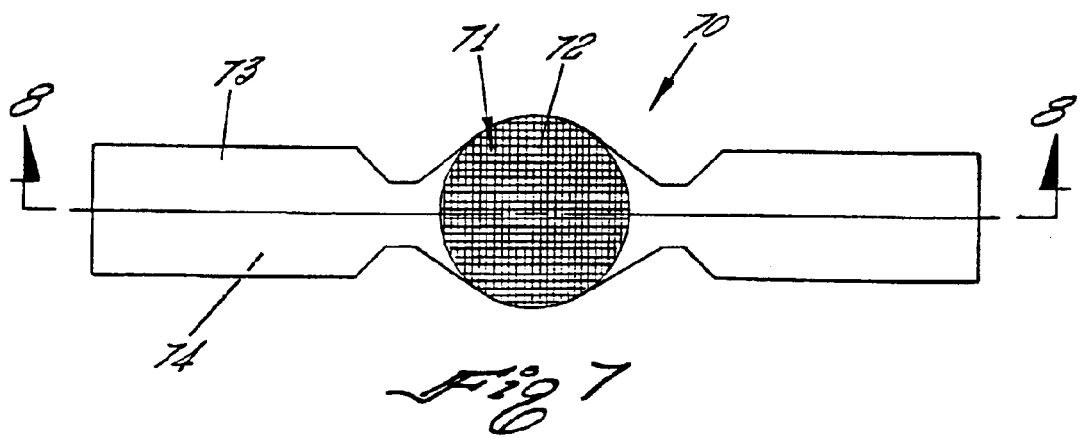
FIG. 7 is a top plan view of an embodiment of a medicament dispensing applicator electrode having unitary construction and an open mesh medicament dispensing portion similar to the embodiment shown in FIGS. 1,3 and adapted for attachment to the skin of a patient.

Turning next to FIG. 7, a second preferred embodiment of a medicament dispensing applicator electrode in accordance with the present invention is shown at 70. The centrally located medicament dispensing portion 71 has cells 72 therewithin which cells provide an aperture between the upper surface 73 and the lower skin-contacting surface 74 of the electrode 70. The applicator electrode 70 is shown in cross-section along section lines 8—8 in FIG. 8. The central medicament dispensing portion 71 of the electrode 70 is mesh-like in construction. A plurality of vertical cells 72 are molded within the elastomer strip comprising the applicator electrode to form apertures which communicate between the upper surface 73 and the lower surface 74. A fluid or semi-fluidic vehicle containing a medicament is placed within the cells 72 which cells are dimensioned to retain the medicament therewithin until an electrical current is passed therethrough. An adhesive layer 75 is coated upon the lower surface 74 of the applicator electrode. The adhesive is chosen to be hypoallergenic, biocompatible and to releasably affix the electrode 70 to the skin.

A bottom view of the applicator electrode of FIGS. 7 and 8 is shown in FIG. 9. In use, the embodiment of the applicator electrode 70 shown in FIGS. 7–9 is affixed to the skin via the adhesive surface 75. The iontophoresis handpiece 40 is grasped between the fingers of the patient such that the tactile electrode (42 in FIG. 5) is in contact with at least one of the patient's fingers. The handpiece is then advanced to the medicament dispensing portion 71 of the applicator electrode 70 until it makes contact therewith. The circuit formed between the fingers grasping the tactile electrode 42 portion of the handpiece 40 and the lesion is made through the mesh surface of the medicament dispensing portion of the applicator electrode. Current flows through the handpiece to the medicament dispensing electrode and into the skin of the patient to return to the handpiece via the fingers and the tactile electrode to close the circuit. As the current flows through the medicament dispensing electrode the current drives the medicament into the skin of the patient.

Figure 12:
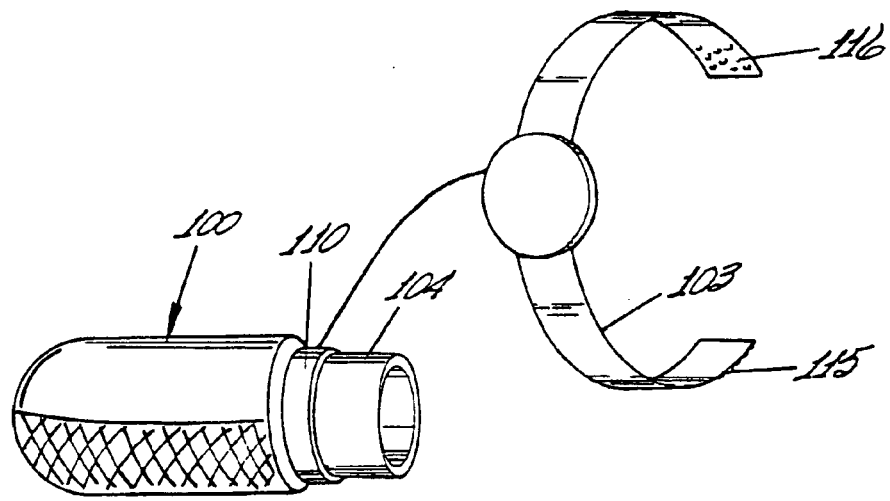
FIG. 12 is a partially cut-away view of the iontophoresis applicator electrode of FIGS. 10 and 11 showing the relationship between the applicator electrode, an insulating finger cot and a wrist-worn adaptation of the iontophoresis device shown in FIG. 4.

Turning now to FIG. 10, a thimble-like medicament-dispensing applicator electrode 100 is shown attached to a finger 105 of the patient. The applicator electrode 100 is in electrical communication with one pole (cathode or anode) of a wrist-worn, bipolar iontophoresis divice 101 by means of a wire 102. The bottom 106 or wrist-facing, skin-contacting surface of the bipolar iontophoresis device 101 is the other pole (anode or cathode) comprising a conductive electrode. The iontophoresis device 101 is releasably affixed to the wrist by means of a strap 103. The iontophoresis device 101 may be constructed similarly to the iontophoresis handpiece 40 except that the working electrode 110 is attached to the wire 102 and the tactile electrode 42 replaced with a conductive electrode 106 forming the skin-contacting portion of the device 101 which is in contact with the wrist of the patient. The applicator electrode 100 is electrically isolated from the finger 105 by means of an insulating finger cot 104. Current from the iontophoresis divice 101 passes through the conductive wire 102 to the working electrode 110 (FIG. 11) to which the wire is conductively attached by means of solder. The electrode 110 has an overlying silicone elastomeric thimble 111. The elastomeric thimble 111 is homogeneous in composition and has an upper surface 112 and a lower surface 113 which comprises a mesh 113a has integral therewith a plurality of retaining cells 114, which cells extend between the electrode 110 and the lower surface 113 and are dimensioned to contain a medicament. In operation, current from the iontophoresis device 101 passes through the wire 102 to the electrode 110 of the applicator electrode. The voltage applied to the electrode 110 drives medicament contained within the cells 114 of the mesh 113 into the skin of a user's body. The current passes through the user's body to the conductive electrode (not shown) which comprises the wrist-facing portion of the iontophoresis device 101. The iontophoresis device 101 preferably includes a power source, a voltage multiplier, a driver and an on/off switch as shown in the handpiece 40, but reconfigured to be worn on the wrist. An enlarged perspective view of the applicator electrode 100 overlying a finger cot is shown in structural relationship in FIG. 12.

The simple design is capable of retaining and dispensing existing medicament formulations and the size of the retaining cells 72 in the mesh portion of the electrode may be varied. The structural matrix of the applicator electrode is a flexible hypoallergenic, non-electrically-conductive material. A suitable material is Silastic®, a silicone elastomer which is biocompatible, non-conductive, flexible and possessing sufficient structural rigidity to contain medicaments and a delivery vehicle within the retaining cells 114. Further, Silastic silicone elastomer is inert so that medicaments will not oxidize or otherwise have their chemical structures damaged. An electrode constructed from silicone elastomer has a prolonged shelf-life, is soft and pleasant on contact, is hypoallergenic and sufficiently flexible to adhere to any anatomical contour such as presented by a thimble. Such anatomical plasticity is a key advantage to the foregoing design. Other polymers, such as polyurethane, are suitable as well. A hydrated hydrophilic cotton layer (not shown) may be interposed between the medicament dispensing portion 71 and the electrically conductive surface 41 of the handpiece 40 to provide pretreatment hydration of the medicament dispensing portion or the mesh may be hydrated by the patient immediately prior to use.

With reference to the embodiment of an iontophoresis applicator electrode shown in FIGS. 7,9, the electrode is easily manufactured using mold technology wherein uncured silicone elastomer is either poured into a complementary mold or pressure-mold injected. The lower surface 74 of the non-medicament dispensing portion of the electrode is coated with skin adhesive. The medicament dispensing portion 71 functions as a medicament reservoir and is preferably between 1 mm and 4 mm thick, depending upon the amount of medicament required to be stored in the cells 72. The medicament-retaining cells 72, which are preferably a hexagonal, honey comb-like structure, retain the medicament therein through their surface tension. Hexagonal cells also lessen cross channel conductivity by means of their vertical orientation. The size and geometry of these cells can vary. The smallest cells, for instance, would be more suited to retaining liquid medicaments while the larger cells are better adapted to retain ointment-based medicaments. Medium cells are more suited to retaining and dispensing gel medicaments and lotions. The silicone walls of the cells can be chemically modified to change the hydrophobic surface characteristics thereof and further improve retention of specially formulated liquid medicaments. For additional cell stability and retention capabilities, the skin-facing surface of the cells can be covered with non-wicking, fibrous and porous materials commonly used in electrodes. A composite or unitary construction from a single mold can be used depending on production cost, it is inexpensive to manufacture and it offers both a compartment for storage of existing formulations as well as a structural backbone for the application electrode. The surface treatments of the retaining material bounding each of the cells to create hydrophilic or hydrophobic surface effects depending on the formulation to be utilized is well known in the art. An example of such technology is disclosed, for example, in U.S. Pat. No. 5,589,563. For ointments and hydrophobic materials, silicone is preferred. For water or gel medicaments, surface treatment such as doping the elastomeric cell surface with hydrophilic molecules can be of additional benefit, as described herein. The embodiments disclosed herein present the following advantages:

Inexpensive manufacture;

Use of either injection or pour molding production;

Use of composite sheet cutout assembly;

Anatomically conforming;

Elastomer surface modification for optimum retention of medicament;

Variable retaining cell size;

Variable retaining cell geometry;

Ability to utilize existing medicament formulations;

May use a cotton or (other hydrophilic matrix) layer for rapid pre-treatment hydration.

May be used with single or multi-channel dispersive iontophoretic drivers; and

May be used with iontophoretic or ionosonic devices.

Figure 13:
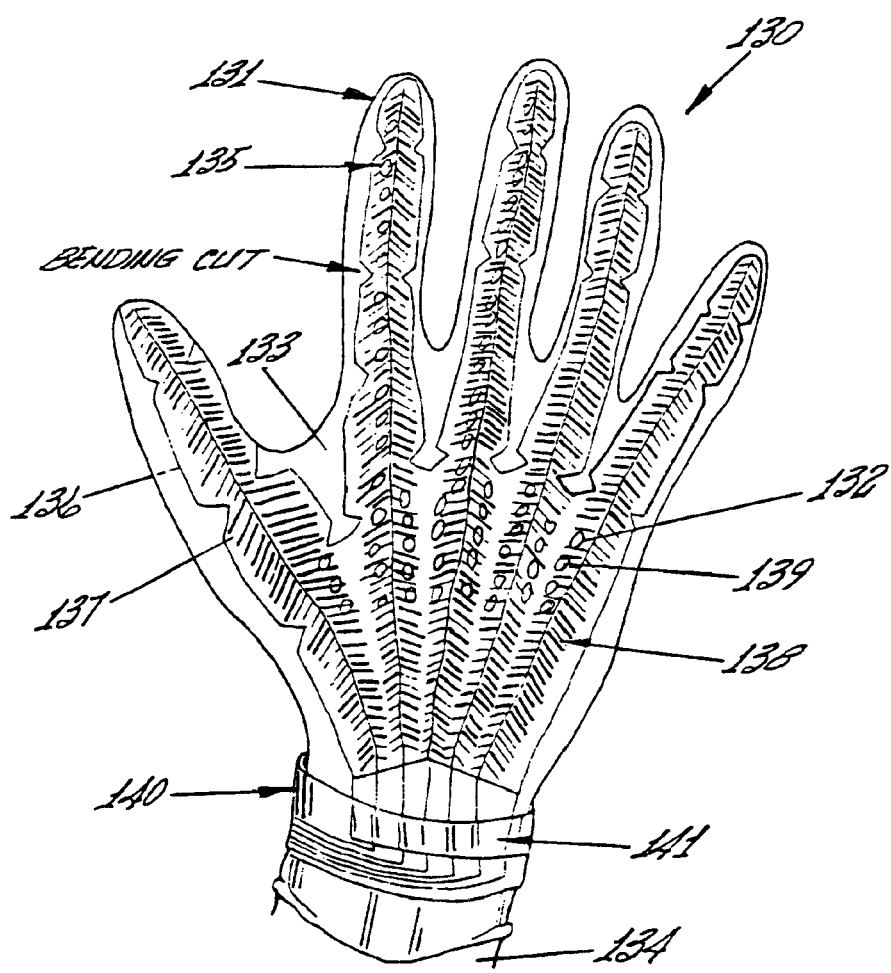
FIG. 13 is a plan view of a glove embodiment of the present invention having a large area electrode.
Figure 14:
FIG. 14 is a perspective view of a patient using the glove embodiment of FIG. 13 to self-administer a medicament to a relatively large portion of skin underlying the glove, as in, for example, the treatment of acne.

An embodiment of the present invention adapted for delivering medicament to a large area of skin is shown in FIG. 13. The iontophoresis electrode is contained within a glove adapted to conform to and be worn upon a patient's hand. The glove embodiment 130 of the iontophoresis drug delivery electrode comprises an elastomeric glove 131 having a plurality of holes or open pores 132 in the palmar surface 133 thereof Underlying the palmar surface 133 and disposed within the glove between the skin 134 and glove is an electrically insulating sheet 135 having an inner surface 136 and an outer surface 137, both of which surfaces are coated with an electrically conductive layer 138. The inner conductive layer 136 is, in use, in electrical communication with the skin. The outer conductive layer 137 is in contact with the interior surface of the glove and the pores 132. A medicament 139 capable of iontophoretic transdermal delivery is contained within the pores. A bipolar power source 140 has a working electrode 141 in electrical communication with the outer conductive layer 137 coating the electrically insulating sheet 135, and a ground electrode (not shown) which is in electrical communication with the inner conductive layer coating the electrically insulating sheet. When the power source 140 is energized, an electrical current flows between the inner conductive layer and the outer conductive layer, which layers are separated by the electrically insulating sheet, via the patient's skin. The polarity and amplitude of the current flowing through pores into the user's skin facilitates entry of the medicament into the skin. The glove embodiment, shown in use in FIG. 14, is particularly useful for transdermally delivering medicament to large areas of skin.

The advantages of a unitary iontophoresis electrode and a glove and finger cot embodiment of an iontophoresis electrode for drug delivery have been presented. It is noted that similarly constructed electrodes may be employed for non-invasively collecting molecular species from the blood. For example, the mesh may be impregnated with an electrically conductive gel. The polarity of the gel, with respect to the skin, may be employed to transport blood components through the skin into the gel where such components may be detected and/or quantitated. Such measurements are useful for monitoring blood levels of compounds such as glucose or drugs.

While the invention has been described above with references to specific embodiments thereof, it is apparent that many changes, modifications and variations in the materials, arrangements of parts and steps can be made without departing from the inventive concept disclosed herein. For example, an impregnated conductive gel can also be used to as medicament containing medium to increase the physical stability and the tissue adhering characteristics of the electrode. Accordingly, the spirit and broad scope of the appended claims is intended to embrace all such changes, modifications and variations that may occur to one of skill in the art upon a reading of the disclosure. All patent applications, patents and other publication cited herein are incorporated by reference in their entirety.

What I claim is:

1. A method of treatment by electrokinetic self-administration of a medicament into a treatment site for an individual, comprising:

providing a device shaped in part to conform to at least a portion of an individual's finger and having a self-contained power source, first and second electrodes, and a substrate in electrical contact with said first electrode along a first surface of said substrate and an exposed contact surface opposite said first surface;

providing said substrate with one of an electrokinetically transportable medicament or a medicament with an electrically conductive carrier therefor;

releasably retaining the divice on the individual's finger with the first electrode interposed between the individual's finger portion and the substrate;

providing an electrical insulator between said first electrode and the individual's finger portion;

while the device remains retained of the individual's finger, placing the contact surface of said substrate into contact with the individual's treatment site;

contacting the individual's body with said second electrode at a location other than the treatment site; and causing electrical current to flow through said first electrode, the medicament or conductive carrier therefor, the treatment site, the individual's body, said second electrode and said power source to electrokinetically drive the medicament into the treatment site.

2. A method according to claim 1 including providing said device with a concave surface for contact about the individual's finger.

3. A method according to claim 1 including providing said first electrode with a convex surface portion for contact with the first surface of said substrate, and providing said exposed contact surface of said substrate in an arcuate convex shape.

4. A method according to claim 1 wherein the step of contacting the individual's body with said second electrode includes contacting the second electrode with the individual's arm.

* * * * *